(12) United States Patent
Xu (10) Patent No.: US 12,404,303 B2
(45) Date of Patent: Sep. 2, 2025

(54) POLYPEPTIDE AND USE THEREOF (71) Applicant: NANJING ANJI BIOLOGICAL TECHNOLOGY CO., LTD., Nanjing (CN)

(72) Inventor: Hanmei Xu, Nanjing (CN)

(73) Assignee: NANJING ANJI BIOLOGICAL TECHNOLOGY CO., LTD., Nanjing (CN)

( * ) Notice: Subject to any disclaimer, the term of this patent is extended or adjusted under 35 U.S.C. 154(b) by 632 days.

(21) Appl. No.: 17/635,990

(22) PCT Filed: Oct. 26, 2020

(86) PCT No.: PCT/CN2020/123555
§ 371 (c)(1),
(2) Date: Feb. 16, 2022

(87) PCT Pub. No.: WO2021/037292
PCT Pub. Date: Mar. 4, 2021

(65) Prior Publication Data
US 2022/0281916 A1   Sep. 8, 2022

(30) Foreign Application Priority Data
Aug. 27, 2019   (CN) .......................... 201910799291.8

(51) Int. Cl.
*C07K 7/08* (2006.01)
*A61P 11/00* (2006.01)
*A61P 31/04* (2006.01)
*C07K 7/06* (2006.01)
*A61K 38/00* (2006.01)

(52) U.S. Cl.
CPC ................ *C07K 7/08* (2013.01); *A61P 11/00* (2018.01); *A61P 31/04* (2018.01); *C07K 7/06* (2013.01); *A61K 38/00* (2013.01)

(58) Field of Classification Search
None
See application file for complete search history.

(56) References Cited

FOREIGN PATENT DOCUMENTS

| CN | 102268068 A | * | 12/2011 |
| CN | 102268070 A | | 12/2011 |
| CN | 102268080 A | * | 12/2011 |
| CN | 104045718 A | * | 9/2014 |
| CN | 110437311 A | | 11/2019 |
| WO | WO2008023336 A2 | * | 2/2008 |

* cited by examiner

*Primary Examiner* — Maury A Audet (57) ABSTRACT

The present disclosure discloses use of a polypeptide, relating to the field of biopharmaceuticals. The polypeptide comprises the following domains: Pro-Arg-Cys-X-Y-Gly-Glu, where X is Trp or Tyr, and Y is Arg or Cys; and Arg-Gly-Ala-Asp-Arg-Ala; or a sequence of any amino acid mutated in the foregoing domains. The polypeptide can be used for treating various fibrosis diseases and symptoms, including pulmonary fibrosis, hepatic fibrosis, myelofibrosis, renal fibrosis, myocardial fibrosis, skin fibrosis, and lung tissue lesions.

5 Claims, 4 Drawing Sheets

Specification includes a Sequence Listing.

SEQUENCE LISTING

```
<160> NUMBER OF SEQ ID NOS: 13

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Arg Gly Ala Asp Arg Ala Gly Gly Gly Pro Arg Cys Trp Arg Gly
1               5                   10                  15

Glu

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Arg Gly Ala Asp Arg Ala Gly Gly Gly Pro Arg Cys Trp Cys Gly
1               5                   10                  15

Glu

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Arg Gly Ala Asp Arg Ala Gly Gly Gly Pro Arg Cys Tyr Arg Gly
1               5                   10                  15

Glu

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Arg Gly Ala Asp Arg Ala Gly Gly Gly Pro Arg Cys Tyr Cys Gly
1               5                   10                  15

Glu

<210> SEQ ID NO 5
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (4)..(4)
<223> OTHER INFORMATION: Xaa is Trp or Tyr
<220> FEATURE:
<221> NAME/KEY: UNSURE
<222> LOCATION: (5)..(5)
<223> OTHER INFORMATION: Xaa is Arg or Cys

<400> SEQUENCE: 5
```

```
Pro Arg Cys Xaa Xaa Gly Glu
1               5
```

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

```
Arg Gly Ala Asp Arg Ala
1               5
```

<210> SEQ ID NO 7
<211> LENGTH: 7
<212> TYPE: PRT
<213> ORGANISM: Artificial Sequence
<220> FEATURE:
<223> OTHER INFORMATION: Synthetic

<400> SEQUENCE: 7

```
Pro Arg Cys Trp Arg Gly Glu
1               5
```

<210> SEQ ID NO 8
<211> LENGTH: 7
<212> TYPE: PRT
<213> ORGANISM: Artificial Sequence
<220> FEATURE:
<223> OTHER INFORMATION: Synthetic

<400> SEQUENCE: 8

```
Pro Arg Cys Tyr Arg Gly Glu
1               5
```

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

```
Pro Arg Cys Trp Cys Gly Glu
1               5
```

<210> SEQ ID NO 10
<211> LENGTH: 7
<212> TYPE: PRT
<213> ORGANISM: Artificial Sequence
<220> FEATURE:
<223> OTHER INFORMATION: Synthetic

<400> SEQUENCE: 10

```
Pro Arg Cys Tyr Cys Gly Glu
1               5
```

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

```
Arg Gly Ala Asp Arg Ala Gly Gly Gly Gly
1               5                   10
```

```
<210> SEQ ID NO 12
<211> LENGTH: 4
<212> TYPE: PRT
<213> ORGANISM: Artificial Sequence
<220> FEATURE:
<223> OTHER INFORMATION: Synthetic

<400> SEQUENCE: 12

Gly Gly Gly Gly
1
```

```
<210> SEQ ID NO 13
<211> LENGTH: 17
<212> TYPE: PRT
<213> ORGANISM: Artificial Sequence
<220> FEATURE:
<223> OTHER INFORMATION: Synthetic
<220> FEATURE:
<221> NAME/KEY: UNSURE
<222> LOCATION: (7)..(7)
<223> OTHER INFORMATION: Xaa is Gly, Ser or other amino acids.
<220> FEATURE:
<221> NAME/KEY: UNSURE
<222> LOCATION: (8)..(8)
<223> OTHER INFORMATION: Xaa is Gly, Ser or other amino acids.
<220> FEATURE:
<221> NAME/KEY: UNSURE
<222> LOCATION: (9)..(9)
<223> OTHER INFORMATION: Xaa is Gly, Ser or other amino acids.
<220> FEATURE:
<221> NAME/KEY: UNSURE
<222> LOCATION: (10)..(10)
<223> OTHER INFORMATION: Xaa is Gly, absent or other amino acids.
<220> FEATURE:
<221> NAME/KEY: UNSURE
<222> LOCATION: (14)..(14)
<223> OTHER INFORMATION: Xaa is Trp or Tyr
<220> FEATURE:
<221> NAME/KEY: UNSURE
<222> LOCATION: (15)..(15)
<223> OTHER INFORMATION: Xaa is Arg or Cys

<400> SEQUENCE: 13

Arg Gly Ala Asp Arg Ala Xaa Xaa Xaa Xaa Pro Arg Cys Xaa Xaa Gly Glu
1               5                   10                  15
```

POLYPEPTIDE AND USE THEREOF

TECHNICAL FIELD

The present disclosure relates to the field of biophaiinaceuticals, and in particular, to a polypeptide which can be used to prevent or treat various fibrosis diseases, and therapeutic use includes anti-pulmonary fibrosis, anti-hepatic fibrosis, anti-myelofibrosis, anti-renal fibrosis, anti-myocardial fibrosis, and anti-skin fibrosis.

BACKGROUND

Fibrosis is defined as excessive deposition of extracellular matrix (ECM) components such as fibronectin (FN) and type I collagen (COLI) by organ fibroblasts. Organ fibrosis is an ultimate common pathway of many diseases leading to end-stage organ failure. Uncontrolled wound healing responses (including acute and chronic inflammation, angiogenesis, activation of fibroblasts and remodeling of extracellular matrix) are involved in the pathogenesis of fibrosis. At present, the pathogenesis, diagnostic methods and preventive measures of organ or tissue fibrosis have been extensively studied. Although considerable progress has been made in some aspects in the prior art, some key problems remain unresolved.

It is learned that organ or tissue fibrosis is implemented in such a way that many causes (such as inflammation, immunity, and poison) parenchymal cell damage, then lead to inflammatory degeneration and necrosis of parenchymal cells, and activate corresponding cells, so that the cells release various cytokines and growth factors (such as TGF-β1 and VEGF); these factors activate resting extracellular matrix producing cells and transform the cells into myofibroblasts; and the myofibroblasts proliferate in large numbers and secrete a large number of cytokines, which then act on macrophages by paracrine. The myofibroblasts can synthesize a large number of ECM components such as collagen, and in addition, the degradation of the ECM is reduced, resulting in organ or tissue fibrosis. Therefore, the occurrence and progression of organ or tissue fibrosis is the result of the interaction of cells, cytokines, ECM, and the like and the involvement of many factors. The main causes are closely related to extracellular matrix (including abnormal changes of matrix metalloproteinases) and abnormal angiogenesis.

1. Pulmonary Fibrosis

Pulmonary fibrosis is a process of excessive repair of lung tissue. Wilson pointed out that when a problem occurs to any one or more links in an "injury-inflammation-repair" chain, the occurrence of fibrosis is caused. At present, the occurrence of pulmonary fibrosis may be attributed to the following three stages: (1) Injury stage: Alveolar epithelial cells are damaged by the stimulation of gas, dust, infection (bacteria or virus), drugs, radiation damage and other factors; (2) Effect stage: Injury promotes the apoptosis of alveolar epithelial cells and leads to oxidative stress response. Inflammatory cells (macrophages, T/B lymphocytes, neutrophils, and the like) recruited at an injury site and a large number of secreted transforming growth factor-β (TGF-β) stimulate the proliferation and differentiation of fibroblasts and promote the formation of lung fibroblast foci; (3) Fibrosis stage: The formation of fibroblast foci and excessive secretion of the ECM lead to the gradual replacement of parenchymal cells of lung tissue by interstitial cells, so that lung tissues lose elasticity and the hardness increases, and finally physiological functions of lung tissues are lost, resulting in that a patient dies due to respiratory failure caused by fibrosis.

A plurality of kinds of cells, such as pulmonary epithelial cells, endothelial cells, pulmonary inflammatory cells (mainly macrophages), and pulmonary interstitial cells (fibroblasts and myofibroblasts), are involved in the occurrence of fibrosis, and the pulmonary interstitial cells are key effector cells for the occurrence of pulmonary fibrosis. In addition, cytokines secreted by cells, such as transforming growth factor-β (TGF-β), a platelet-derived growth factor (PDGF), a basic fibroblast growth factor (BFGF), a connective tissue growth factor (CTGF), an insulin-like growth factor (IGF), a vascular endothelial growth factor (VEGF), integrin, matrix metalloproteinase (MMP), and an inhibitor (TIMP) thereof, also have a profound impact on the occurrence of pulmonary fibrosis.

The most critical cytokine is TGF-β. TGF-β is a multifunctional cell growth factor that can regulate cell proliferation and differentiation. The proliferation of a large number of myofibroblasts and the excessive accumulation of the ECM can be stimulated by directly stimulating the activation of in situ fibroblasts or through endothelial-mesenchymal transition (EnMT) and epithelial-mesenchymal transition (EMT) processes. When TGF-β is continuously activated due to damage, MAPK, EGF, and Wnt/β-catenin signals are cross-activated, leading to the progression of fibrosis. The PDGF, the BFGF, and the VEGF as growth factors can promote the proliferation and differentiation of lung fibroblasts, and affect the progression of pulmonary fibrosis. The MMP/TIMP is a main regulator of the ECM, and the contents of the two play a key role in the balance of the ECM. These cytokines have a more or less influence on the proliferation and activation of lung fibroblasts and the formation of collagen, and therefore reasonable regulation of cytokine expression facilitates the treatment of pulmonary fibrosis.

The polypeptide designed according to the present disclosure has dual functions of a matrix metalloproteinase (MMP) inhibitor and inhibition of angiogenesis, and combines the MMP inhibitor with an angiogenesis inhibitor. The MMP inhibitor starts with regulating the ECM and the key cytokines MMP/TIMP in lung injury, an angiogenesis inhibitor can inhibit the release of cytokines such as TGF-β1 and VGFE, can inhibit the proliferation and activation of fibroblasts, and can act on the treatment of pulmonary fibrosis from the main pathogenesis in pathology.

2. Hepatic Fibrosis

Hepatic fibrosis is the repair response of the liver to chronic liver injury caused by various causes, and mainly features excessive deposition of ECM. Hepatic fibrosis is a common pathological feature of various chronic liver diseases, and is a main intermediate link of further progression to cirrhosis, or even malignant transformation and death. It is extremely difficult to treat cirrhosis and the mortality is high, but it is currently considered that hepatic fibrosis is reversible. Therefore, blocking or delaying the occurrence and progression of hepatic fibrosis has important application value for the treatment of various chronic liver diseases accompanying hepatic fibrosis. At present, clinically, the treatment of hepatic fibrosis includes etiological treatment of a primary disease and treatment of fibrosis itself. However, removing a cause of the primary disease cannot completely inhibit the progression of hepatic fibrosis, and the existence of fibrosis may further affect the therapeutic effect on the primary disease. Therefore, the treatment of fibrosis is particularly important. However, a mechanism of occurrence and progression of hepatic fibrosis is very complicated. At present, the research mainly focuses on the activation and transformation of hepatic stellate cells into myofibroblasts and fibroblasts. Possible ways are activation of a TGF-β signal transduction pathway, a PDGF receptor-mediated signal transduction pathway, a TNF-α-mediated signal transduction pathway, cyclooxygenase-2 (COX-2), diffuse ECM, angiogenesis, oxidative stress-mediated hepatic fibrosis, or the like.

At present, anti-hepatic fibrosis drugs under study function mainly by inhibiting or alleviating inflammatory response, resisting oxidative stress, inhibiting the activation and proliferation of hepatic stellate cells that play a major role in the process of hepatic fibrosis or promoting apoptosis of the hepatic stellate cells, protecting hepatocytes, promoting liver regeneration, inhibiting or neutralizing activity of fibrosis promotion factors, inhibiting angiogenesis, and inhibiting the synthesis of extracellular matrix or promoting degradation of the extracellular matrix. In recent decades, although some progress has been made in the research of anti-hepatic fibrosis drugs, many drugs, such as a TGF-β1 antagonist, a hepatocyte growth factor, S-adenosylmethionine, and pirfenidone, are still in a preclinical or clinical trial stage, and no chemical drug has been approved for the treatment of human hepatic fibrosis.

3. Renal Fibrosis

Renal fibrosis (including renal interstitial fibrosis and glomerulosclerosis) is the main pathological basis of the final stage of renal damage caused by various causes. A mechanism of renal fibrosis is relatively complicated and related to many factors, and is mainly related to proliferation and activation of extracellular matrix producing cells and transformation imbalance of vasoactive substances, cytokines and extracellular matrix. Renal interstitial fibrosis is a common pathway for almost all primary or secondary renal diseases to progress to end-stage renal failure.

At present, most drugs for the treatment of renal fibrosis have problems such as high toxicity, low safety, and single pharmacological actions.

Polypeptide drugs have higher druggability than general chemical drugs, have high biological activity, high specificity and relatively weak toxic reaction, and do not easily accumulate in the body. A polypeptide may be designed according to its pathogenesis, is under a multi-target design, and can inhibit the occurrence of renal fibrosis in multiple ways.

4. Myelofibrosis

Referred to as MF, Myelofibrosis is a myeloproliferative disease caused by the proliferation of collagen in hematopoietic tissue of bone marrow, with its fibrous tissue seriously affecting a hematopoietic function. Primary myelofibrosis is also referred to as "myelosclerosis" and "myeloid metaplasia of an unknown cause". This disease features different degrees of proliferation of bone marrow fibrous tissue, and extramedullary hematopoiesis mainly occurring in the spleen, followed by liver and lymph nodes. Typical clinical manifestations are erythroblastic anemia and promyelocyte anemia, with more teardrop-shaped erythrocytes, dry aspiration often occurs in bone marrow puncture, the spleen often obviously swells, and osteosclerosis of different degrees is presented. This disease is a rare disease with an incidence of 0.2/100000 to 2/100000. The onset age is mostly between 50 years old and 70 years old, and the disease may also be seen in infants, with the incidence in males slightly higher than that in females.

Myelofibrosis indicates that fibroblasts and TGF-β1 and other fibrosis-related mechanisms are involved. Many mutant genes found are related to inflammatory pathways, indicating that inflammatory response is also involved in the occurrence and progression of myelofibrosis. In fact, in existing studies, it is reported that increased expression of inflammatory cytokines, increased expression of lysyl oxidase (LOX), increased expression of TGF-β1, impaired functions of megakaryocytes and activation of abnormal JAK-STAT signaling pathways are involved in the pathogenesis of myelofibrosis. An important feature of myelofibrosis is the increase in level of inflammatory cytokines. An important factor is TGF-β1, which plays an important role in fibrosis. The level of TGF-β1 in bone marrow of a patient with myelofibrosis increases significantly. In a patient with myelofibrosis, extracellular matrix accumulates, fibers proliferate, and a large number of new vessels form.

5. Myocardial Fibrosis

Myocardial fibrosis is cardiac interstitial remodeling that features excessive proliferation of cardiac interstitial fibroblasts and excessive deposition and abnormal distribution of collagen. Pathologically, myocardial fibrosis mainly features increased collagen deposition, proportion imbalance of different kinds of collagen, and especially increased proportion and disordered arrangement of type I and type III collagen, accompanied by proliferation of myocardial fibroblasts. Myocardial fibrosis is closely related to a variety of cardiovascular diseases, such as hypertension, chronic heart failure, and dilated cardiomyopathy, and is a potential risk factor of sudden cardiac death. The expression of matrix metalloproteinases in a patient with myocardial fibrosis increases, and factors related to angiogenesis also shows high expression. At present, the specific pathogenesis of myocardial fibrosis is not very clear. It is mainly believed that myocardial fibrosis is closely related to a renin-angiotensin-aldosterone system, various cytokines, oxidative stress, and the like. These factors affect the occurrence and progression of myocardial fibrosis through the same or different conduction pathways.

At present, no marketed drug for treating myocardial fibrosis is available, and therefore it is necessary to develop a drug for treating myocardial fibrosis.

6. Skin Fibrosis

Skin fibrosis is excessive scar formation of skin and a result of pathological wound healing response. Skin fibrosis has the features that the function and structure of small vessels are abnormal, skin and internal organs are in a fibrosis state, and an immune system is in an activation state. For many years, scholars at home and abroad have made in-depth research on the mechanism of scar occurrence, progression and regression from multiple angles and levels, but up to now, no clear conclusion is reached on its mechanism, and no effective way for prevention and treatment is available. Relatively consistent views are as follows: ① Fibroblasts are main effector cells of skin fibrosis, which are characterized by excessive cell proliferation and excessive deposition of the extracellular matrix. ② Collagen metabolism disorder is a main biological manifestation of the skin fibrosis. ③ A TGF-β1/Smad signaling pathway is closely related to a plurality of physiological and pathological processes such as proliferation, differentiation, migration, apoptosis, and collagen metabolism of fibroblasts. Smads regulate collagen metabolism of fibroblasts bidirectionally according to different types.

The most common method used to treat skin fibrosis is immunosuppressive therapy. The basic principle is that autoimmune causes inflammation of diseases and subsequent tissue damage and fibrosis. Commonly used drugs include methotrexate, cyclophosphamide, and cyclosporine. Although some improvements in immunosuppressive therapy have been observed, concerns about the safety of the drugs and the lack of confirmed clinical data and demonstrable efficacy still exist. Therefore, it is necessary to develop an effective pharmaceutical preparation for the treatment of skin fibrosis, fibrotic skin diseases and pathological scar formation of the skin.

7. Lung Tissue Lesions

Many diseases may form extensive multifocal or diffuse lesions in the lungs. All diseases that cause interstitial lung diseases or parenchymal double-lung extensive lesions are collectively referred to as diffuse lung diseases. Pathogenic causes include infection, inhalation, tumor drug reactivity, vascular connective tissue diseases, respiratory diseases, and some diseases of unknown causes. Most of the lung diseases are caused by chronic inflammation, and are treated by using an anti-inflammatory method, an anti-oxidation method, and other methods.

SUMMARY

The Sequence Listing created on Apr. 4, 2022 with a file size of 4.00 KB, and filed herewith in ASCII text file format as the file entitled "Sequence_Listing-G204RAYT0004US.TXT," is hereby incorporated by reference in its entirety

1. To-Be-Resolved Problem

In view of a situation in which most of existing drugs for treating fibrosis are chemical drugs, and the chemical drugs have problems such as high toxicity, low safety, and a single pharmacological target, the present disclosure provides use of a polypeptide, which has a good therapeutic effect on lung fibrosis, hepatic fibrosis, renal fibrosis, myocardial fibrosis, myelofibrosis, skin fibrosis, and lung tissue lesions. The polypeptide according to the present disclosure contains a plurality of domains, can target a plurality of targets, and can inhibit the occurrence of fibrosis in multiple ways.

2. Technical Solutions

To resolve the foregoing problems, technical solutions adopted by the present disclosure are as follows:

A polypeptide, where the polypeptide comprises the following domains:

Pro-Arg-Cys-X-Y-Gly-Glu (see SEQ ID NO: 5), where X is Trp or Tyr, and Y is Arg or Cys; and Arg-Gly-Ala-Asp-Arg-Ala (see SEQ ID NO: 6);

or a sequence of any amino acid mutated in the foregoing domains.

That is, the polypeptide contains the following domains:

Pro-Arg-Cys-Trp-Ara-Gly-Glu, (see SEQ ID NO: 7)

Pro-Arg-Cys-Tyr-Ara-Gly-Glu, (see SEQ ID NO: 8)

Pro-Arg-Cys-Trp-Cys-Gly-Glu, (see SEQ ID NO: 9)

Pro-Arg-Cys-Tyr-Cys-Gly-Glu, (see SEQ ID NO: 10) and

Arg-Gly-Ala-Asp-Arg-Ala-Gly-Gly-Gly-Gly. (see SEQ ID NO: 11)

The polypeptide is linked by a linker, and the linker is a flexible linker composed of Gly-Gly-Gly-Gly (see SEQ ID NO: 12), Ser-Ser-Ser or other amino acids, that is, Arg-Gly-Ala-Asp-Arg-Ala-linker-Pro-Arg-Cys-X-Y-Gly-Glu (see SEQ ID NO: 13).

The amino acid sequence of the polypeptide is the following amino acid sequence or an amino acid sequence with 80% homology therewith:

Arg-Gly-Ala-Asp-Arg-Ala-linker-Pro-Arg-Cys-X-Y-Gly-Glu (see SEQ ID NO: 13);

polypeptide I: Arg-Gly-Ala-Asp-Arg-Ala-Gly-Gly-Gly-Gly-Pro-Arg-Cys-Trp-Arg-Gly-Glu (see SEQ ID NO: 1);

polypeptide II: Arg-Gly-Ala-Asp-Arg-Ala-Gly-Gly-Gly-Gly-Pro-Arg-Cys-Trp-Cys-Gly-Glu (see SEQ ID NO: 2);

Polypeptide III: Arg-Gly-Ala-Asp-Arg-Ala-Gly-Gly-Gly-Gly-Pro-Arg-Cys-Tyr-Arg-Gly-Glu (see SEQ ID NO: 3); and polypeptide IV Arg-Gly-Ala-Asp-Arg-Ala-Gly-Gly-Gly-Gly-Pro-Arg-Cys-Tyr-Cys-Gly-Glu (see SEQ ID NO: 4); and use of the polypeptide in the preparation of anti-pulmonary fibrosis, anti-hepatic fibrosis, anti-renal fibrosis, anti-myocardial fibrosis, anti-myelofibrosis and anti-skin fibrosis drugs and drugs for resisting lung tissue lesions is provided.

Preferably, the lung tissue lesions include bacterial pneumonia, viral pneumonia, *mycoplasma* pneumonia, fungal pneumonia, *chlamydia* pneumonia, and protozoal pneumonia.

The polypeptide according to the present disclosure has double targets, and has double effects of the MMP inhibitor and the angiogenesis inhibitor. The polypeptide reduces the activation of fibroblasts and the deposition of extracellular matrix, can slow down the fibrosis process, and can further inhibit the infection of various lung diseases.

3. Beneficial Effects

Compared with the prior art, the present disclosure has the following beneficial effects:

(1) The polypeptide according to the present disclosure can be used for treating various fibrosis diseases, including pulmonary fibrosis, hepatic fibrosis, renal fibrosis, myocardial fibrosis, skin fibrosis, and myelofibrosis. Components of the polypeptide are all natural amino acids, which are easy to synthesize, have no obvious toxic or side effects, and have high safety.

(2) In an animal model for treating pulmonary fibrosis, the polypeptide according to the present disclosure can improve the lung tissue structure, reduce inflammatory response, reduce the score of pulmonary fibrosis, obviously improve a situation of pulmonary fibrosis, and prolong a life cycle of an animal.

(3) The polypeptide according to the present disclosure can inhibit the proliferation and activation of fibroblasts and hepatic stellate cells and the generation of HYP.

(4) In the animal model for treating renal fibrosis, the polypeptide according to the present disclosure can significantly reduce the expression content of TGF-$\beta$1 in renal tissues and significantly improve a situation of renal fibrosis.

(5) The polypeptide according to the present disclosure can inhibit the proliferation of cardiac fibroblasts of rats.

(6) The polypeptide according to the present disclosure can inhibit the process of myelofibrosis and reduce the expression content of TGF-$\beta$1.

(7) The fused polypeptide according to the present disclosure can be used for treating skin fibrosis. In a skin fibrosis model, the polypeptide can significantly reduce the expression content of HYP in skin and significantly improve a situation of skin scar hyperplasia.

(8) The polypeptide according to the present disclosure also has a good inhibitory effect on the infection of lung diseases, and the inhibitory rate is 60% or above.

(9) The polypeptide according to the present disclosure is a multi-target drug, and can inhibit the process of fibrosis in multiple ways.

DESCRIPTION OF EMBODIMENTS

Polypeptides I, II, III and IV were Synthesized by GenScript (Nanjing) Co., Ltd.

Embodiment 1 Pulmonary Fibrosis Animal Model

Experimental Animals and Materials:
1. Experimental Animals:
   Source and strain: SPF level, SD rats, provided by Shanghai Xipuer-Bikai laboratory Animal Co., Ltd. (laboratory animal license: SCXK (hu) 2013-0016)
   Weight: 180-200 g at the time of purchase and 180-220 g at the beginning of modeling.
   Gender: Male.
   Number of animals in each group: 14 animals in each group.
2. Experimental Materials:
   Bleomycin Manufacturer: Zhejiang Han Hui Pharmaceutical Co., Ltd.
   Pharmaceutical Co., Ltd.
   Normal saline Manufacturer: Anhui Double Crane Pharmaceutical Co., Ltd.
   Chloral hydrate Manufacturer: Sinopharm Chemical Reagent Co., Ltd.
   BIBF1120 (Nintedanib) Manufacturer: Jinan Synovel Chemical Co., Ltd.
   Tissue fixative Manufacturer: Wuhan servicebio Co., Ltd.
3. Experimental Method:
   SD rats were anesthetized by intraperitoneal injection of 1 mL/100 g 4% chloral hydrate. After anesthesia, the rats were fixed and their necks were disinfected by using cotton with 75% alcohol. The skin of the rat neck was longitudinally cut with scissors, and the fascia and muscle were longitudinally bluntly torn with tweezers to expose the trachea. A syringe was inserted into the trachea to inject 5 mg/kg bleomycin, while a blank group was injected with an equal amount of normal saline. Then a rat plate was quickly erected and rotated, the rats' breathing was observed, the neck wound was sterilized after rotation and was sewn, and an amoxicillin anti-inflammatory drug was sprinkled on the suture. After the operation, the rats were put back into a dry and clean cage for resting, waiting was performed for awakening. The rats were awakened after about 1-2 hours, and then fed normally. On the $7^{th}$ day after modeling, modeling group animals randomly fell into a model group, a Nintedanib positive drug group, polypeptide I, II, III and IV dosage groups, and a normal control group, and the groups were administered separately for an administration cycle of 14 days. Living situations of rats were observed every day and their weights were weighed. After administration for 14 days, the rats were dissected, the lungs were taken, and the superior lobe of right lung was taken and placed in a tissue fixative, embedded, and sliced, HE-stained and Masson-stained.
4. Experimental Grouping and Dosage Setting

TABLE 1

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Twice a day | 14 |
| Model group | Normal saline | 0.5 mL/200 g | Subcutaneous injection | Twice a day | 14 |

TABLE 1-continued

Experimental grouping and dosage regimen

| Group | Drug | Dosage | Administration mode | Administration frequency | Quantity |
|---|---|---|---|---|---|
| Positive drug | Nintedanib | 25 mg/kg | Intragastric administration | Once a day | 14 |
| Test drug (1) | Polypeptide I | 7.5 mg/kg | Subcutaneous injection | Twice a day | 14 |
| Test drug (2) | Polypeptide II | 7.5 mg/kg | Subcutaneous injection | Twice a day | 14 |
| Test drug (3) | Polypeptide III | 7.5 mg/kg | Subcutaneous injection | Twice a day | 14 |
| Test drug (4) | Polypeptide IV | 7.5 mg/kg | Subcutaneous injection | Twice a day | 14 |

5. Experimental Results
1. Impact of a Polypeptide on the Survival Rate of SD Rats Induced By Bleomycin As shown in Table 2, compared with the survival rate (64.3%) of SD rats in the model group, the survival rate of SD rats in each test drug group was higher than that of the model group, and each test drug could significantly increase the survival rate of SD rats. The survival rates of the polypeptide II group and the positive drug group were equal (85.7%), the survival rates of the polypeptide I group and the polypeptide III group were 78.6%, and the survival rate of the polypeptide IV group was 92.9%.

TABLE 2

Impact of a polypeptide on survival rate (%) of SD rats with bleomycin-induced pulmonary fibrosis

| Group | Dosage (mg/kg) | Number of animals at the beginning | Number of animals at the end | Survival rate (%) |
|---|---|---|---|---|
| Blank group | | 14 | 14 | 100 |
| Model group | | 14 | 9 | 64.3 |
| Positive drug | 25 | 14 | 12 | 85.7 |
| Polypeptide I | 7.5 | 14 | 11 | 78.6 |
| Polypeptide II | 7.5 | 14 | 12 | 85.7 |
| Polypeptide III | 7.5 | 14 | 11 | 78.6 |
| Polypeptide IV | 7.5 | 14 | 13 | 92.9 |

Figure 1:
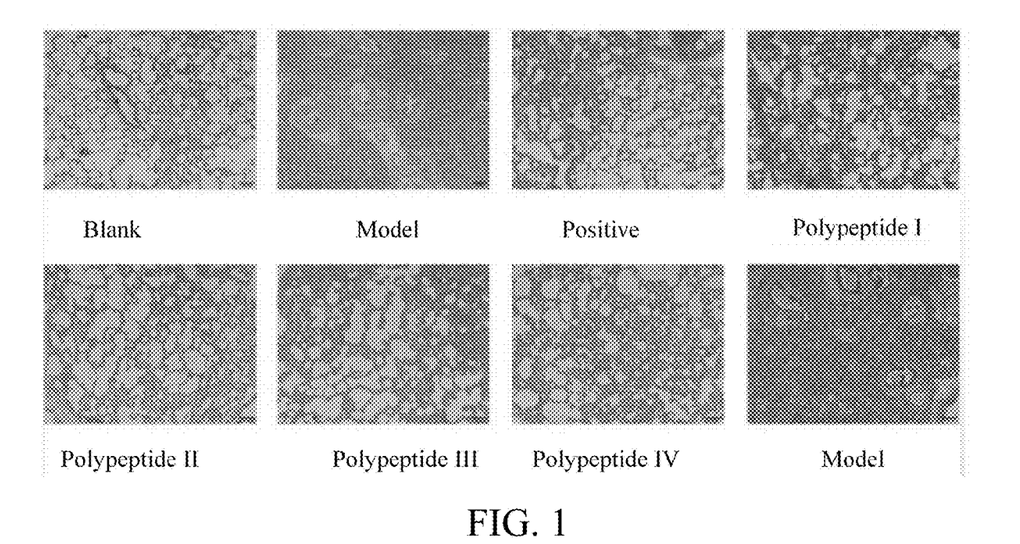
FIG. 1 is a diagram of HE staining of lung tissues with polypeptides I, II, III and IV according to the present disclosure.
Figure 2:
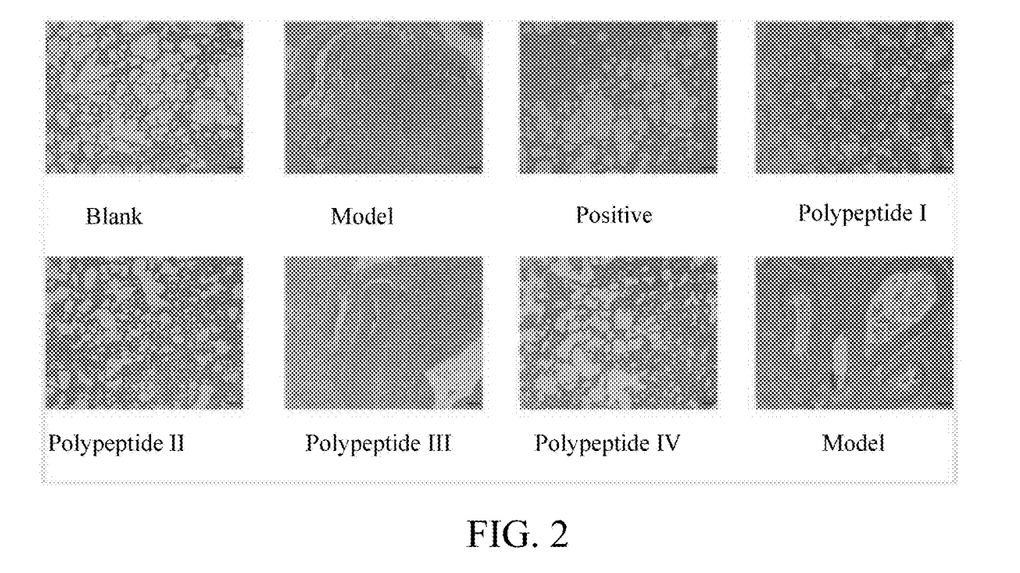
FIG. 2 is a diagram of Masson staining of lung tissues with polypeptides I, II, III and IV according to the present disclosure.

2. Pathological Analysis of a Polypeptide on Bleomycin-Induced Pulmonary Fibrosis in SD Rats Research results showed that a pulmonary fibrosis model in SD rats was successfully established in this study. Main manifestations of lung tissue lesions are fibroblast proliferation and collagen fiber formation in the alveolar wall and mesenchyme around intrapulmonary bronchi and vascular branches. Masson staining showed blue-green staining reaction, and inflammatory cell infiltration, congestion in the alveolar wall, cell degeneration disorder and other lesions occurred. After administration, the degree of pulmonary fibrosis and other lesions were less than those in the model group. See FIG. 1 and FIG. 2 for HE staining and Masson staining.

Embodiment 2 Establishment of an In Vitro Hepatic Fibrosis Model and Treatment with a Polypeptide 1. Experimental Materials:
Alkaline HYP kit Manufacturer: Nanjing Jiancheng Bioengineering Institute 2. Experimental Method:

LX-2 cells were cultured in 1640 medium containing 10% FBS, and cultured in an incubator with 5% $CO_2$ at 37° C. The medium was replaced every two days, and subcultured according to the cell density. The LX-2 cells in a logarithmic growth phase were digested with 0.25% pancreatin to make cell suspension. The density of the cells was adjusted to $4 \times 10^5$ cells/mL, and the cells were inoculated into 96-well plates with 100 μL per well and cultured overnight. On the second day, TGF-β1 was added to induce the proliferation and activation of the LX-2 cells, and the polypeptide drugs were administered at 1 μmol/L. TGF-β1 (10 ng/mL) was added to each group except the blank group. The cells were cultured in the incubator for 48 hours, and then 10 μL of MTT was added to each well. The MTT was removed after 4 hours, and 150 μL of DMSO was added for reaction for 5 min. An OD value was measured by a microplate reader at 570 nm.

Determining of HYP content in cells: LX-2 cells were cultured in 1640 medium containing 10% FBS, and then cultured in an incubator with 5% $CO_2$ at 37° C. The medium was replaced every two days and subcultured according to the cell density. The LX-2 cells in a logarithmic growth phase were digested with 0.25% pancreatin to make cell suspension. The density of the cells was adjusted to $2.5 \times 10^5$ cells/mL, and the cells were inoculated into 6-well plates with 1 mL per well and cultured overnight. On the second day, TGF-β1 (10 ng/mL) was added to induce the activation of the cells, and the polypeptide was added for intervention. No TGF-β1 was added for induction except the blank group. After being cultured for 48 hours, the cells were collected, and the expression content of HYP in LX-2 cells was measured by using an HYP kit.

3. Experimental Results
(1) Impact of a Polypeptide on the Proliferation of LX-2 Cells Induced by TGF-β1

TGF-β1 can induce the proliferation and activation of LX-2 cells and promote the activation of hepatic stellate cells. After administration of polypeptide drugs, the proliferation and activation of LX-2 cells could be inhibited. Results are shown in Table 3. The inhibitory effect of polypeptide II was the most significant, and the polypeptide II group was highly significantly different from the model group (**$P<0.01$), and the polypeptide I group, the polypeptide III group and the polypeptide IV group were significantly different from the model group (*$P<0.05$).

TABLE 3

Impact of a polypeptide on the proliferation of
LX-2 cells induced by TGF-β1

| Group | OD value |
|---|---|
| Blank group | 0.5 ± 0.02*** |
| Model group | 0.81 ± 0.03 |
| Polypeptide I | 0.66 ± 0.02* |
| Polypeptide II | 0.59 ± 0.02** |
| Polypeptide III | 0.63 ± 0.03* |
| Polypeptide IV | 0.64 ± 0.03* |

*P < 0.001, P < 0.01 vs model;

(2) Impact of a Polypeptide on the HYP Content of LX-2 Cells Induced by TGF-β1

Figure 3:
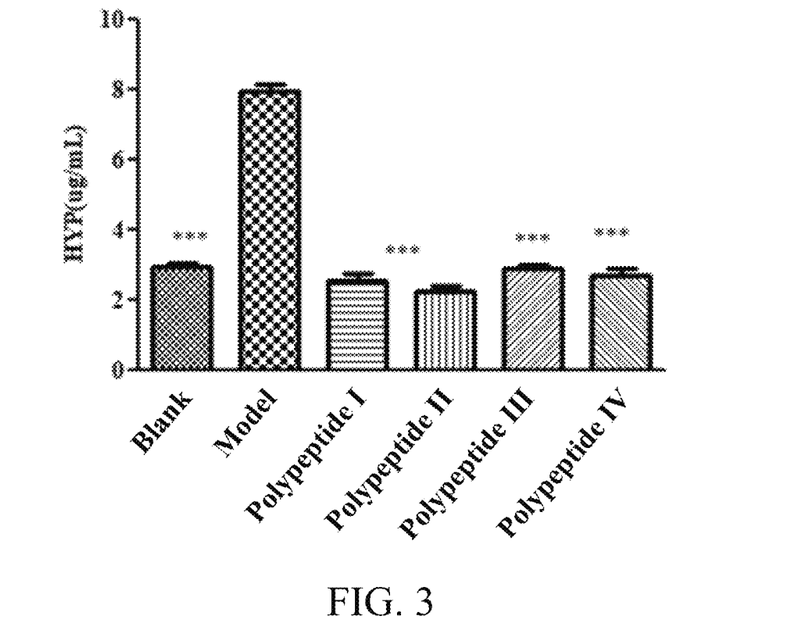
FIG. 3 is a diagram showing that polypeptides I, II, III and IV according to the present disclosure can lower the HYP content in hepatic stellate cells.

Experiments on human body specimens show that a large amount of collagen is accumulated in the interstitial tissue with hepatic fibrosis, and the content of collagen reflects the level of hepatic fibrosis. Hydroxyproline accounts for 13.4% of collagen. Therefore, the content of hydroxyproline can reflect the accumulation of collagen in the process of hepatic fibrosis, and therefore reflect the degree of hepatic fibrosis. As shown in FIG. 3, after administration of polypeptide drugs, the content of HYP could be significantly inhibited, and the process of fibrosis could be inhibited.

Embodiment 3 Establishment of a Renal Fibrosis Model

1. Experimental Animals

Clean grade male SD rats, purchased from Nanjing Qinglong Mountain Animal Farm, and weighed 180-200 g at the time of purchase, 190-210 g at the beginning of modeling, and 180-200 g at the beginning of administration.

2. Experimental Materials:

Normal saline Manufacturer: Anhui Double Crane Pharmaceutical Co., Ltd.

Rat TGF-β1 ELISA kit Manufacturer: Tianjin Annuo Ruikang Biotechnology Co., Ltd.

Alkaline HYP kit Manufacturer: Nanjing Jiancheng Bio-engineering Institute

3. Experimental Method

A renal fibrosis animal model was established. SD rats were anesthetized with 4% chloral hydrate, injected with 1 mL/100 g intraperitoneally, fixed to an operation board, and sterilized in an operation area for later use. The abdominal cavity was cut open about 3-4 mm to the left of the ventrimeson, left kidney ureter was separated in an operation group, the ureter was ligated and separated close to the ureter near the lower pole of the inferior pole of kidney, and the ureter was cut short between two ligations after the double ligations. Muscular layers and abdominal walls were sewed layer by layer, the suture was disinfected with alcohol. After SD rats woke up, the rats were put into a cage for feeding. In the blank group, ureter was not ligated, and other steps were the same.

Then, the animals fell into a blank group, a model group, and polypeptide administration groups, and the administration was started on the second day after the operation, twice a day for 14 days. After administration for 14 days, blood was taken and supernatant was taken to detect the content of TGF-β1 in serum.

4. Experimental Grouping and Dosage Setting

TABLE 4

Experimental grouping and dosage regimen

| Group | Drug | Dosage | Administration mode | Administration frequency | Quantity |
|---|---|---|---|---|---|
| Blank group | Normal saline | 0.5 mL/200 g | Subcutaneous injection | Once a day | 10 |
| Model group | Normal saline | 0.5 mL/200 g | Subcutaneous injection | Once a day | 10 |
| Test drug (1) | Polypeptide I | 7.5 mg/kg | Subcutaneous injection | Twice a day | 10 |
| Test drug (2) | Polypeptide II | 7.5 mg/kg | Subcutaneous injection | Twice a day | 10 |
| Test drug (3) | Polypeptide III | 7.5 mg/kg | Subcutaneous injection | Twice a day | 10 |
| Test drug (4) | Polypeptide IV | 7.5 mg/kg | Subcutaneous injection | Twice a day | 10 |

Figure 4:
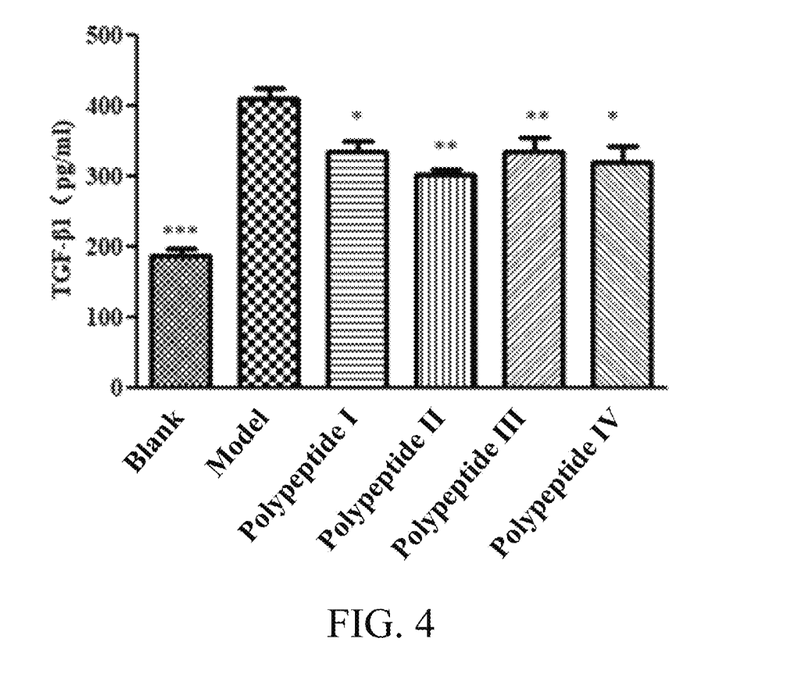
FIG. 4 is a diagram showing that polypeptides I, II, III and IV according to the present disclosure can lower the TGF-$\beta$1 content in a renal fibrosis model.

5. Experimental Results (1) Impact of a Polypeptide on the Content of TGF-β1 in Serum of SD Rats with Renal Fibrosis TGF-β1 is the most important fibrogenic factor. In renal fibrosis, the expression of TGF-β1 was significantly increased. The result is shown in FIG. 4, and there was a highly significant difference between the model group and the blank group (*P<0.001). After administration, all groups could significantly reduce the content of TGF-β1 in serum, and the polypeptide II group was highly significantly different from the model group (*P<0.001), and the polypeptide I group, the polypeptide III group and the polypeptide IV group were highly significantly different from the model group (**P<0.01).

Embodiment 4 In Vitro Myocardial Fibrosis Model

1. Experimental Method

The inhibitory effect of a polypeptide on cardiac fibroblasts of rats was detected by MTT assay. Cells were cultured in a DMEM medium containing 10% of FBS, the cytoplasm was made into $1\times10^5$/mL cell suspension, and 100 μL per well was inoculated into a 96-well plate. After the cells adhered to the wall, the medium was replaced with a serum-free DMEM medium, and the serum-free medium was discarded after 24 hours. The cells were cultured with different polypeptides of 1 μmol/L, and 5 multiple wells were set for each concentration. After 12, 24 and 48 hours separately, 10 μL of MTT was added to each well. After 4 hours, MTT was sucked out, and 150 μL of DMSO was added to each well. After reaction for 5 min, an OD value was measured at 570 nm by a microplate reader.

blood was used for peripheral blood analysis, some blood was centrifuged, and the supernatant was taken to measure the content of TGF-β1 in the serum of mice.

4. Experimental Grouping and Dosage Regimen

TABLE 6

Experimental grouping and dosage regimen

| Group | Drug | Dosage | Administration mode | Administration frequency | Times of administration |
|---|---|---|---|---|---|
| Blank group | Normal saline | 0.2 mL | Subcutaneous injection | Twice a day | 56 times |
| Model group | Normal saline | 0.2 mL | Subcutaneous injection | Twice a day | 56 times |
| Test drug (1) | Polypeptide I | 10 mg/kg | Subcutaneous injection | Twice a day | 56 times |
| Test drug (2) | Polypeptide II | 10 mg/kg | Subcutaneous injection | Twice a day | 56 times |
| Test drug (3) | Polypeptide III | 10 mg/kg | Subcutaneous injection | Twice a day | 56 times |
| Test drug (4) | Polypeptide IV | 10 mg/kg | Subcutaneous injection | Twice a day | 56 times |

2. Experimental Results

At 24 hours and 48 hours, polypeptides I, II, III and IV could inhibit the proliferation of cardiac fibroblasts of rats at 1 μmol/L. The results are shown in Table 5.

TABLE 5

Impact of a polypeptide on the proliferation of cardiac fibroblasts of rats

| Group | Optical density values at different time points | | |
|---|---|---|---|
| | 12 hours | 24 hours | 48 hours |
| Blank group | 0.335 ± 0.001 | 0.454 ± 0.018 | 0.698 ± 0.006 |
| Polypeptide I (1 μmol/L) | 0.326 ± 0.006 | 0.392 ± 0.008*** | 0.580 ± 0.012*** |
| Polypeptide II (1 μmol/L) | 0.325 ± 0.004 | 0.377 ± 0.015*** | 0.518 ± 0.015*** |
| Polypeptide III (1 μmol/L) | 0.329 ± 0.012 | 0.402 ± 0.012** | 0.612 ± 0.018* |
| Polypeptide IV (1 μmol/L) | 0.309 ± 0.010 | 0.385 ± 0.008** | 0.598 ± 0.013* |

*$P < 0.001$, $P < 0.01$, *$P < 0.05$ vs control.

Embodiment 5 Establishment of a Myelofibrosis Model

1. Experimental Animals

Female Kunming mice aged 4 weeks, purchased from Nanjing Qinglong Mountain Animal Farm.

2. Experimental Materials:

Rh EPO for injection Manufacturer: Shanghai Clonbiotech. Co., Ltd.

Mouse TGF-β1 ELISA kit Manufacturer: Tianjin Annuo Ruikang Biotechnology Co., Ltd.

3. Modeling Method

There were 10 mice in each group. The normal control group was injected with normal saline (0.3 mL for each mouse), and the remaining groups were injected with rh EPO (0.1 unit/gram, body weight, 0.3 mL for each mouse) intraperitoneally every day. After induction for two days, drug therapy was started, subcutaneous injection was given twice a day, and after continuous administration for 28 days, the mouse heart was punctured for blood extraction, some 5. Experimental Results (1) Analysis of Peripheral Blood Cells in Each Group The number of white blood cells in the model group was significantly higher than that in the normal control group, and the number of white blood cells also decreased compared with that in the model group after administration, but there was no significant difference. The levels of Hb, MCV and RDW in the model group significantly increased and were highly significantly different from those in the blank group ($P<0.01$). The expression levels of Hb, MCV and RDW could be decreased after administration, which was significantly different from in the model group ($P<0.5$). The results are shown in Table 7.

TABLE 7

Analysis of peripheral blood cells in each group

| Group | WBC | Hb | MCV | RDW |
|---|---|---|---|---|
| Blank | 5.59 ± 1.02 | 125 ± 23** | 48 ± 3** | 23 ± 2** |
| Model | 6.26 ± 2.01 | 225 ± 76 | 67 ± 4 | 37 ± 4 |
| Polypeptide I | 5.97 ± 1.76 | 143 ± 23* | 52 ± 4* | 31 ± 2* |
| Polypeptide II | 5.61 ± 1.43 | 151 ± 19* | 51 ± 9* | 26 ± 3* |
| Polypeptide III | 5.79 ± 1.23 | 145 ± 17* | 53 ± 8* | 28 ± 1* |
| Polypeptide IV | 5.83 ± 1.07 | 155 ± 16* | 54 ± 5* | 24 ± 1* |

**$P < 0.01$, *$P < 0.05$ vs model.

(2) Impact of a Polypeptide on the Content of TGF-β1 in Mouse Serum

Figure 5:
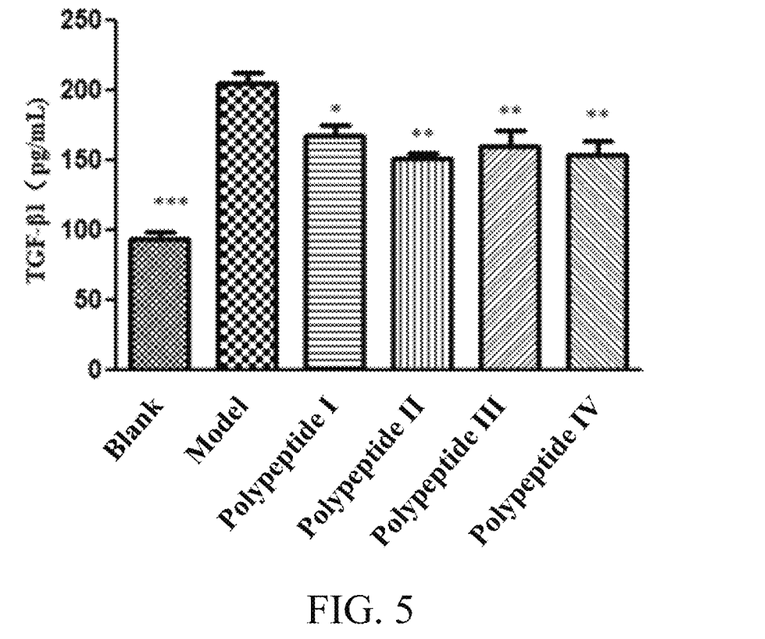
FIG. 5 is a diagram showing that polypeptides I, II, III and IV according to the present disclosure can inhibit the TGF-$\beta$1 content in a myelofibrosis model.

TGFβ1 is the most important fibrogenic factor. In myelofibrosis, the expression of TGF-β1 was significantly increased. The result is shown in FIG. 5, and there was a highly significant difference between the model group and the blank group (*$P<0.001$). After administration, all groups could significantly reduce the content of TGF-β1 in serum, and the polypeptides II group were highly significantly different from the model group (*$P<0.001$), and the polypeptide I group, the polypeptide III group and the polypeptide IV groups were highly significantly different from the model group (**$P<0.01$).

Embodiment 6 Establishment of a Skin Fibrosis Model

1. Experimental Animals
   Male C57/BL black mice aged 6-8 weeks, purchased from Nanjing Qinglong Mountain Animal Farm.
2. Experimental Materials
   Bleomycin Manufacturer: Zhejiang Han Hui Pharmaceutical Co., Ltd.
   Pharmaceutical Co., Ltd.
   Normal saline Manufacturer: Anhui Double Crane Pharmaceutical Co., Ltd.
   Rat TGF-β1 ELISA kit Manufacturer: Tianjin Annuo Ruikang Biotechnology Co., Ltd.
   Alkaline HYP kit Manufacturer: Nanjing Jiancheng Bioengineering Institute
3. Modeling Method
   Bleomycin (10 μg/mL) was injected subcutaneously every day for 28 days to form skin fibrosis. During the modeling period, the administration groups were given polypeptide drugs every day for treatment, with 10 mice in each group. After modeling, the mice were killed on the next day, and the skin tissue of the mouse back was taken to detect the content of HYP in the skin tissue.
4. Experimental Grouping and Dosage Regimen

TABLE 8

Experimental grouping and dosage regimen

| Group | Drug | Dosage | Administration mode | Administration frequency |
| --- | --- | --- | --- | --- |
| Blank group | Normal saline | 0.2 mL | Subcutaneous injection | Twice a day |
| Model group | Normal saline | 0.2 mL | Subcutaneous injection | Twice a day |
| Test drug (1) | Polypeptide I | 10 mg/kg | Subcutaneous injection | Twice a day |
| Test drug (2) | Polypeptide II | 10 mg/kg | Subcutaneous injection | Twice a day |
| Test drug (3) | Polypeptide III | 10 mg/kg | Subcutaneous injection | Twice a day |
| Test drug (4) | Polypeptide IV | 10 mg/kg | Subcutaneous injection | Twice a day |

Figure 6:
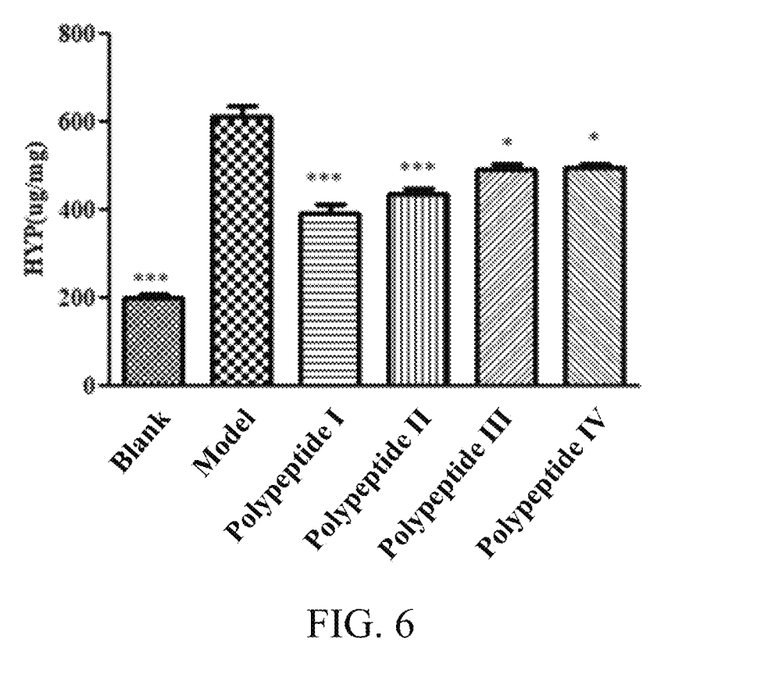
FIG. 6 shows that fused polypeptides I, II, III and IV according to the present disclosure inhibit the expression content of HYP in a skin fibrosis model.

5. Experimental Results
(1) Expression of HYP Content in the Skin Tissue of Each Group of Mice The content of hydroxyproline in the skin tissue of the mouse back was detected. As the characteristic protein of collagen, hydroxyproline can reflect the content of collagen in the skin tissue from the side. As shown in FIG. 6, each polypeptide group could reduce the expression of HYP in the skin tissue. The polypeptide I group and the polypeptide II group could significantly reduce the expression of HYP in the lung tissue, and were highly significantly different from the model group (***$P<0.001$). The polypeptide III group and the polypeptide IV group could reduce the content of HYP in the lung tissue of SD rats, and were highly significantly different from the model group (*$P<0.05$).

Figure 7:
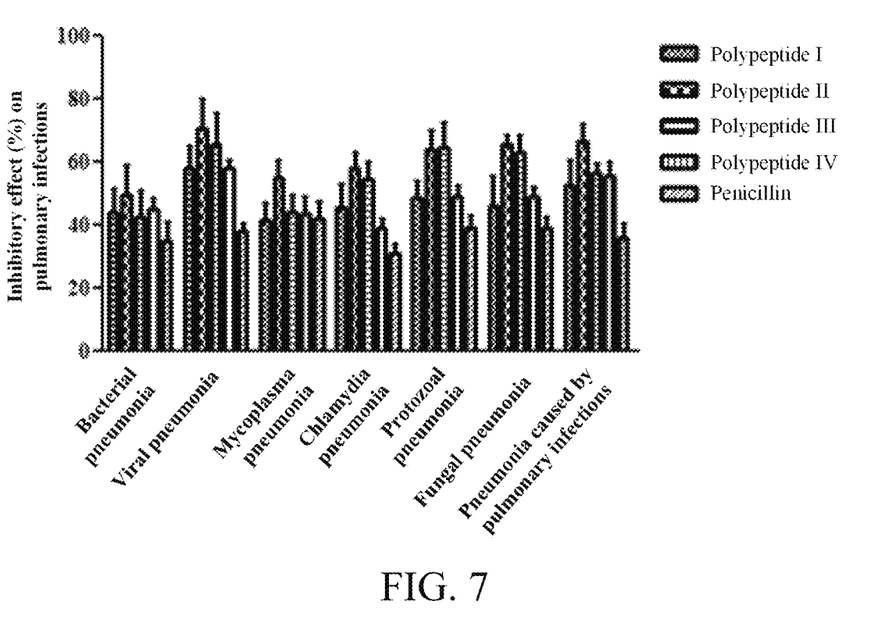
FIG. 7 shows an inhibitory effect of polypeptides I, II, III and IV according to the present disclosure on pulmonary infections.

Embodiment 7 Inhibitory Effect of a Polypeptide According to the Present Disclosure on Multiple Pulmonary Infections A mouse pneumonia model was successfully established by using a nasal drip method. BALB/C mice with a body weight of 18-24 g were selected, and then anesthetized with ether on day 0, day 1 and day 2, respectively, prepared *streptococcus pneumoniae* bacteria solution, adenovirus concentrated solution, *mycoplasma pneumoniae, chlamydia pneumoniae,* protozoa and pneumonia fungi were slowly dropped into the nasal cavity of the mice, so that the bacteria solutions entered the trachea and bronchi, and the bacteria solutions were prevented from flowing into the esophagus during the operation to avoid inactivation of the bacteria solutions, so that the mouse pneumonia model was established. After the model was successfully established, the polypeptide according to the present disclosure was administered, as shown in FIG. 7 and Table 9. The results showed that compared with the drug in the penicillin administration group, the polypeptide according to the present disclosure had a more significant improvement effect on a plurality of lung infections. The experimental results are represented on the basis of average values±standard deviation.

TABLE 9

Inhibitory effect of a polypeptide according to the present disclosure on multiple pulmonary infections

| Pneumonia type | Polypeptide I | Polypeptide II | Polypeptide III | Polypeptide IV | Penicillin |
| --- | --- | --- | --- | --- | --- |
| Bacterial pneumonia | 43.83 ± 7.59 | 49.25 ± 9.48 | 42.29 ± 8.76 | 45.05 ± 3.25 | 35.05 ± 5.75 |
| Viral pneumonia | 58.00 ± 6.84 | 70.33 ± 9.27 | 65.49 ± 9.94 | 58.07 ± 2.07 | 38.07 ± 2.27 |
| Mycoplasma pneumonia | 41.48 ± 5.55 | 54.69 ± 5.72 | 43.93 ± 5.34 | 43.27 ± 5.63 | 41.77 ± 5.73 |
| Chlamydia pneumonia | 45.18 ± 7.46 | 57.81 ± 5.21 | 54.40 ± 5.41 | 38.85 ± 3.11 | 30.75 ± 3.31 |
| Protozoal pneumonia | 48.16 ± 5.46 | 63.60 ± 6.16 | 64.29 ± 8.07 | 49.04 ± 3.17 | 39.04 ± 3.71 |
| Fungal pneumonia | 45.65 ± 9.68 | 65.32 ± 3.07 | 62.88 ± 5.49 | 48.61 ± 3.22 | 38.61 ± 3.82 |
| Pneumonia caused by pulmonary infections | 52.47 ± 7.88 | 66.15 ± 5.87 | 56.18 ± 3.31 | 55.57 ± 4.25 | 35.67 ± 4.55 |

What is claimed is:

1. A polypeptide comprising the amino acid sequence selected from the group consisting of SEQ ID NO: 1, SEQ ID NO: 2, SEQ ID NO: 3 and SEQ ID: 4:

```
polypeptide I (SEQ ID NO: 1):
Arg-Gly-Ala-Asp-Arg-Ala-Gly-Gly-Gly-Gly-Pro-Arg- Cys-Trp-Arg-Gly-Glu;

polypeptide II (SEQ ID NO: 2):
Arg-Gly-Ala-Asp-Arg-Ala-Gly-Gly-Gly-Gly-Pro-Arg-

Cys-Trp-Cys-Gly-Glu;

Polypeptide III (SEQ ID NO: 3):
Arg-Gly-Ala-Asp-Arg-Ala-Gly-Gly-Gly-Gly-Pro-Arg- Cys-Tyr-Arg-Gly-Glu;
and polypeptide IV (SEQ ID NO: 4):
Arg-Gly-Ala-Asp-Arg-Ala-Gly-Gly-Gly-Gly-Pro-Arg- Cys-Tyr-Cys-Gly-Glu.
``` or a pharmaceutically acceptable salt thereof.

2. A method for reducing fibrosis selected from the group consisting of pulmonary fibrosis, hepatic fibrosis, renal fibrosis, myocardial fibrosis, skin fibrosis, and myelofibrosis, comprising administering, to a subject in need thereof, a therapeutically effective amount of a polypeptide according to claim 1.

3. A method for reducing a lung tissue lesion caused by an infection selected from the group consisting of bacterial pneumonia, viral pneumonia, *mycoplasma* pneumonia, fungal pneumonia, *chlamydia* pneumonia, and protozoal pneumonia, comprising administering, to a subject in need thereof, a therapeutically effective amount of a polypeptide according to claim 1.

4. The method according to claim 2, wherein the polypeptide is administered as a dosage form through a route consisting of an injection, a capsule, a tablet, a nasal spray or an aerosol.

5. The method according to claim 3, wherein the polypeptide is administered as a dosage form through a route consisting of an injection, a capsule, a tablet, a nasal spray or an aerosol.

* * * * *